(12) United States Patent
Elsasser et al.

(10) Patent No.: US 6,623,604 B1
(45) Date of Patent: Sep. 23, 2003

(54) METHOD OF RECOVERING FREE FATTY ACIDS HAVING LOW ESTER CONTENT AND HIGH ACID VALUE

(75) Inventors: A. Fred Elsasser, Cincinnati, OH (US); C. William Blewett, Lakeside Park, KY (US)

(73) Assignee: Cognis Corporation, Gulph Mills, PA (US)

( * ) Notice: Subject to any disclaimer, the term of this patent is extended or adjusted under 35 U.S.C. 154(b) by 199 days.

(21) Appl. No.: 09/586,917

(22) Filed: Jun. 5, 2000

(51) Int. Cl.[7] .............................. B01D 3/00; C09F 5/12; C11B 3/14; C07C 29/80
(52) U.S. Cl. .............................. 203/46; 203/79; 203/80; 203/85; 203/92; 203/96; 530/207; 554/21; 554/175; 554/178; 568/913
(58) Field of Search .................... 203/91–98, 79–80, 203/100, 29, 85, 46; 530/205, 207, 208, 209; 159/16.3; 554/21, 175, 178; 568/913, 918–921

(56) References Cited

U.S. PATENT DOCUMENTS

| | | | |
|---|---|---|---|
| 2,530,810 A | | 11/1950 | Christenson et al. |
| 3,804,819 A | * | 4/1974 | Wengrow et al. ............ 530/208 |
| 3,859,270 A | * | 1/1975 | Zvejnieks .................... 530/206 |
| 4,076,700 A | | 2/1978 | Harada et al. |
| 4,464,305 A | | 8/1984 | Patrick, Jr. |
| 4,524,024 A | | 6/1985 | Hughes |
| 4,534,900 A | | 8/1985 | Cleary |
| 4,615,839 A | | 10/1986 | Seto et al. |
| 5,097,012 A | | 3/1992 | Thies et al. |
| 5,209,826 A | * | 5/1993 | Ozaki et al. .................. 203/38 |
| 5,646,311 A | | 7/1997 | Hunt et al. |

FOREIGN PATENT DOCUMENTS

| | | | |
|---|---|---|---|
| DE | 19742097 | * | 12/1998 |
| SU | 340652 | * | 6/1972 |

* cited by examiner

Primary Examiner—Virginia Manoharan
(74) Attorney, Agent, or Firm—John E. Drach

(57) ABSTRACT

Methods of recovering free fatty acids having a low ester content from alkanol-containing solutions and oil mixtures containing tocopherols are disclosed which involve atmospheric or vacuum stripping at low temperatures. The recovered fatty acids have a high acid value, and have high commercial value in the production of high quality (high acid value) products, e.g., dimerized fatty acids, useful in polyamide resins.

33 Claims, No Drawings

METHOD OF RECOVERING FREE FATTY ACIDS HAVING LOW ESTER CONTENT AND HIGH ACID VALUE

BACKGROUND OF THE INVENTION

1. Technical Field

The present invention relates to methods of recovering free fatty acids from edible oils and more particularly to methods of recovering free fatty acids having a low ester content and high acid value from oils.

2. Description of the Related Art

It is known that edible oils, e.g., vegetable and animal oils, may be deodorized to remove impurities, e.g., volatiles, colored components, and odiferous compounds, to provide oils of higher quality. Deodorization of these oils through water vapor distillation produces steam distillates. A typical steam distillate from a vegetable oil, i.e., vegetable oil distillate, such as soybean oil, contains tocopherols, sterols, fatty acids, glycerides and other components. Among these various components, the tocopherols which include alpha-, beta-, gamma-, and delta-tocopherols, are of commercial value because of their vitamin E activity, i.e., antioxidizing activity. Accordingly, various commercial processes including esterification, saponification, fractional extraction, etc., exist for recovering tocopherols from the steam distillates.

Saponification is a particularly preferred method, since it produces salts of fatty acids (soaps) which can be readily separated from unsaponifiables, e.g., tocopherols and sterols, which are present in the steam distillates, through the use of, e.g., a solvent which dissolves the tocopherols but not the salts, thereby allowing recovery of tocopherols free from fatty acids. Typically, the steam distillate is saponified by heating the distillate with alkali metal hydroxide in an alkanol-water mixture. The saponified mixture is then subjected to solvent extraction using a solvent which extracts the non-saponifiables, e.g., tocopherols and sterols, to produce a phase containing mainly the non-saponifiables and solvent and a raffinate phase containing saponified fatty acids, water, alkali metal hydroxide, alkanol, and the remaining solvent. The phase containing the non-saponifiables, e.g., tocopherols, can then be readily separated from the raffinate phase to provide tocopherols free from fatty acids. The tocopherols can then be further processed for commercial use.

The fatty acids which are a by-product of the tocopherol recovery method, also have commercial value in a wide range of applications which include, inter alia, soaps, foods, cosmetics, paints and protective coatings, lubricating greases and oils, etc. The recovery of free fatty acids from the raffinate phase typically involves acidulation of this phase to produce an aqueous layer containing salt and an organic layer containing the free fatty acids, alkanol, and solvent. The alkanol and solvent are then removed from the organic layer by stripping at relatively high temperatures, e.g., by sending the organic layer through a heat loop having a temperature of about 150° C. prior to sending the organic layer to an atmospheric flash tank. The stripped fatty acids can then be sent through a counter-current stripper with steam to further reduce solvent and alkanol present in the mixture.

A problem encountered in utilizing the aforementioned stripping process is that when the organic layer is sent through the heat loop maintained at relatively high temperatures of about 150° C., the free fatty acids undergo esterification with the alkanols present in the organic layer. The esterification of the fatty acids becomes significant enough to have a detrimental effect on the quality of the resultant fatty acid product. Typically, the free fatty acids recovered from such a stripping process have an ester content of from about 1.5 to about 5.0 weight percent, and an acid value of from about 179 to about 192, whereas a desired acid value ranges from about 194 to about 200. Accordingly, downstream products containing carboxylic acid functionality made from fatty acids of low acid value will also have a low acid value which in turn, reduces the quality and commercial value of such products.

SUMMARY OF THE INVENTION

The present invention addresses and avoids the aforementioned problem, i.e., esterification of fatty acids by stripping at relatively high temperature, by providing methods of recovering free fatty acids having a reduced ester content and increased acid value relative to the ester content and acid value of fatty acids obtained by stripping fatty acid mixtures at relatively high temperatures to remove the alkanol and solvents.

The methods described herein are advantageous in that the recovered fatty acids are a by-product of the aforementioned tocopherol recovery method and as such, offers a less expensive, high quality (high acid value) starting material for production of dimerized fatty acids, isostearic acid, and other commercially valuable products of high quality.

A method for recovering free fatty acids from an alkanol-containing solution of the fatty acids is provided which comprises distilling the alkanol-containing solution under conditions of temperature and pressure sufficient to avoid any appreciable production of fatty acid esters to provide a product containing free fatty acids and no appreciable amount of fatty acid esters.

A method of separating fatty acids from a composition containing at least one non-saponifiable component is also provided which comprises a) subjecting the composition to saponification conditions in the presence of alkali metal hydroxide, alkanol and water to provide a mixture containing at least one non-saponified component and saponified fatty acids, b) separating the mixture by solvent extraction employing a solvent to provide a solvent-rich phase containing the non-saponified component(s) of the mixture and a raffinate phase containing the saponified fatty acids, alkanol, water, the balance of the solvent and alkali metal hydroxide, c) acidifying the raffinate phase to provide an aqueous phase containing water, alkanol, and alkali metal salt and an organic phase containing fatty acids, alkanol, and solvent, and d) distilling the organic phase under conditions of temperature and pressure sufficient to avoid the production of any appreciable amount of fatty acid esters to provide a product containing fatty acids and no appreciable amount of fatty acid esters.

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about".

In one aspect, the invention relates to a method of recovering free fatty acids from an alkanol-containing solution of the fatty acids which includes distilling the alkanol-containing solution under conditions of temperature and pressure sufficient to avoid any appreciable production of fatty acid esters to provide a product containing free fatty acids and no appreciable amount of fatty acid esters. The phrase "free fatty acids" employed herein shall be understood as referring to fatty acids containing unreacted (e.g., unesterified) carboxyl groups which are therefore free to be subsequently reacted in a wide variety of subsequent reactions, e.g., condensation reactions in which polyamides or polyesters are produced. Examples of free fatty acids recovered by the foregoing method include, but are not-limited to, saturated fatty acids such as palmitic acid and stearic acid, unsaturated fatty acids such as oleic acid, linolenic acid, brassidic acid, elaidic acid, palmitoleic acid, erucic acid, arachidonic acid, etc., and mixtures thereof.

The alkanol-containing solution of fatty acids can be derived from any suitable oil mixture known in the art, e.g., saponifiable oil mixtures, which may optionally include tocopherols as described below. Examples of suitable oil mixtures include, but are not limited to, vegetable oils and vegetable oil residues such as soybean oil, corn oil, safflower oil, peanut oil, cottonseed oil, sunflower oil, rapeseed oil, palm oil, linseed oil and other vegetable oils, and animal oils such as fish oil and wool wax. Vegetable and animal oil deodorizer distillates are preferred, and vegetable oil deodorizer distillates are particularly preferred.

Examples of alkanols present in the alkanol-containing solution of fatty acids include, but are not limited to, one or more alkanols selected from the group consisting of methanol, ethanol, propanol, isopropanol, butanol, isobutanol, pentanol and hexanol.

Distillation of the alkanol-containing solution of fatty acids to remove the alkanol is carried out at conditions of temperature and pressure sufficient to avoid any appreciable production of fatty acid esters. Preferably, the alkanol-containing solution is distilled under vacuum or at atmospheric pressure at temperatures significantly below those conventionally employed in the distillation of fatty acid-containing solutions. Generally, vacuum distillation of the alkanol-containing solution of fatty acids can be carried out by evaporating the alkanol from the alkanol-containing solution at a temperature of from about 35 to about 90° C. and a vacuum of from about 50 to about 150 torr and preferably at a temperature of from about 75 to about 90° C. and a vacuum of from about 50 to about 100 torr.

Alternatively, as stated above, the alkanol can be distilled away from the alkanol-containing solution of fatty acids at relatively low temperature and at atmospheric pressure, i.e., atmospheric stripping. Distillation temperatures of from about 85 to about 120° C. at atmospheric pressure are generally maintained, with temperatures of from about 90 to about 115° C. at atmospheric pressure being preferred. Atmospheric stripping at low temperature can be carried out using any standard distillation equipment, and is preferably carried out using an atmospheric stripping column which is well known to those skilled in the art (see Example 5).

The product containing free fatty acids produced by the foregoing method typically possesses a fatty acid ester content of not greater than about 0.5 weight percent and preferably not greater than about 0.1 weight percent, and an acid value of from about 194 to about 200, and preferably from about 196 to about 200.

In another aspect, the foregoing method further includes subjecting the product containing free fatty acids to dimerization reaction conditions to provide a composition comprising dimerized fatty acids. Methods of dimerizing unsaturated fatty acids are well known in the art as described, e.g., in U.S. Pat. Nos. 3,632,822, 3,422,124, 2,793,219, 2,793,220, 2,955,121, and 4,776,983, the contents of each of which are incorporated by reference herein. The dimerization of fatty acids typically involves charging a reaction vessel with unsaturated fatty acid, e.g., oleic acid, and heating the fatty acid at an elevated temperature, e.g., from about 230 to about 270° C., under autogenous pressure, e.g., from about 70 to about 175 psi, in the presence of a mineral clay, and preferably water and an alkali or alkaline earth metal salt, e.g., a lithium salt such as lithium carbonate. The clay serves as a catalyst for promoting dimerization of the fatty acids.

In another aspect, the present invention is directed to a method of separating fatty acids from a composition containing at least one non-saponifiable component, e.g., tocopherol. The fatty acids to be separated from the composition are the same as those described above in the method of recovering free fatty acids from an alkanol-containing solution of the fatty acids. The composition containing the fatty acids and at least one non-saponifiable component can be any suitable oil mixture as described above with vegetable oil deodorizer distillates being preferred. The non-saponifiable component can include tocopherols, sterols, and other neutral-containing substances present in the composition, with tocopherols being preferred.

The composition, e.g., a vegetable oil deodorizer distillate, is a) subjected to saponification conditions in the presence of an alkali metal hydroxide, an alkanol and water to provide a mixture containing at least one non-saponified component and saponified fatty acids. Preferably, the composition is saponified by heating it to a temperature of from about 120 to about 200 ° C. at a pressure of from about 2 to about 20 psig, and more preferably at a temperature of from about 175 to about 185° C. at a pressure of from about 7 to about 10 psig. Examples of alkali metal hydroxides include, but are not limited to, sodium and potassium hydroxide. The alkanols which are utilized to saponify the mixture include, but are not limited to, methanol, ethanol, propanol, isopropanol, butanol, isobutanol, pentanol, hexanol and mixtures thereof, with methanol being preferred.

The mixture is then b) separated by solvent extraction employing a solvent to provide a solvent-rich phase containing the non-saponified component(s) of the mixture and a raffinate phase containing the saponified fatty acids, alkanol, water, the balance of the solvent, and alkali metal hydroxide. Suitable solvents that are useful in dissolving the non-saponified components include, but are not limited to, hydrocarbons such as hexane, cyclohexane, toluene, and heptane and halogenated hydrocarbons such as chloroform, dichloroethane and dichloromethane. The solvent extraction can be carried out at a temperature ranging from room temperature to about 80° C. by using from about 0.5 to about 3 parts by volume of the solvent per volume of the saponified mixture. A raffinate phase obtained from a vegetable oil deodorizer distillate using the alkanol, methanol, and the solvent, dichloroethane, typically contains from about 10 to about 20% saponified fatty acids (soaps), about 10 to about 20% methanol, about 20 to about 30% dichloroethane, about 1 to 2% alkali metal hydroxide and about 40 to about 50% water.

The raffinate phase is then c) acidified using a strong acid, e.g., hydrochloric acid or sulfuric acid, to provide an aqueous phase containing water, alkanol, and alkali metal salt and an organic phase containing fatty acids, alkanol and solvent. The amount of strong acid typically used adjusts the mixtures's pH to about 3.0 to about 3.5.

The organic phase is then d) distilled under conditions of temperature and pressure sufficient to avoid the production of any appreciable amount of fatty acid esters to provide a product containing free fatty acids and no appreciable amount of fatty acid esters. The general and preferred distillation conditions which are utilized to distill away the alkanol and solvent from the organic phase are the same conditions as those utilized in the distillation step of the method of recovering free fatty acids from an alkanol-containing solution of the fatty acids as described above.

Any solvent or volatiles, e.g., hexanol, remaining in the product containing fatty acids can be further reduced by various suitable known methods, e.g., steam stripping, by evaporation in an atmospheric flash tank at a temperature of about 150° C., and preferably by vacuum distillation at a temperature of from about 25 to about 100° C. and at a vacuum of from about 50 to about 150 torr.

The following examples are meant to illustrate but not limit the invention.

EXAMPLE 1

Preparation of Organic Phase Containing Free Fatty Acids, Alkanol, and Solvent From Vegetable Oil Deodorizer Distillate A vegetable oil deodorizer distillate (350.0 grams of soya oil deodorizer distillate with a composition of 27.4% fatty acids, 27.1% triglycerides, 10.3% sterols, 8.0% sterol esters, 9.8% tocopherols, and 17.5% other materials) was added to a mixture of 50% NaOH (66.50 grams) and methanol (390.0 grams) and the mixture was saponified by heating it to a temperature of 175 to 185° C. at a pressure of from 7 to 10 psig for 4 hours. After the saponification was done, water (390.0 grams) was added.

The saponified mixture (300.0 grams) was then treated with dichloroethane (520.0 grams) to yield a solvent-rich phase (500.0 grams) containing tocopherols, sterols and other non-saponifiable material and a raffinate phase (320.0 grams water/methanol layer) consisting of about 17% soaps, 15% methanol, 24% dichloroethane, 1% NaOH and 43% water. The solvent-rich phase containing non-saponified material was separated from the raffinate phase by centrifuge. The raffinate phase was acidified with sulfuric acid and water to a pH of 3 to 3.5 to yield an aqueous phase containing water, methanol and salt, and an organic phase containing fatty acids, methanol, dichloroethane and other organic material. The organic phase contained 35 to 40% fatty acids as determined by proton nuclear magnetic resonance (NNR, Varian Unity 400 NMR), 2 to 3% methanol and 56 to 63% dichloroethane.

EXAMPLE 2

Comparison of Vacuum Stripping at Low Temperature Versus Stripping Using a Heat Loop/ Atmospheric Flash Tank of the Organic Phase To remove solvents present in the organic phase containing fatty acids, a sample of the organic phase prepared as described in Example 1 was either stripped 1) by vacuum using a rotary evaporator at a temperature of 40° C. and a vacuum of 50 torr or 2) by sending the sample through a heat loop heated to 150° C. followed by evaporation in an atmospheric flash tank. A sample from each stripping method was analyzed for acid value and ester content using proton NMR (Varian Unity 400 NMR). The results of these experiments are listed in Table 1 below.

TABLE 1

| SAMPLE CONDITIONS | PERCENT METHYL ESTER | PERCENT ETHYL ESTER | PERCENT OTHER ESTERS | PERCENT DICHLOROETHANE | ACID VALUE |
|---|---|---|---|---|---|
| Vacuum stripped at 40° C. at 150 torr | <0.6 | <0.1 | <0.1 | 2.6 | 198.4 |
| Stripped by passing through heat loop at 150° C. and then evaporated in atmospheric flash tank | 2.0 | 0.6 | 1.3 | 20.2 | 189.3 |

As seen from the data in Table 1, a significant amount of esters are formed in the product by stripping at relatively high temperature (heat loop at 150° C./atmospheric flash tank). The ester content of the organic phase sample which was subjected to vacuum stripping at lower temperature and vacuum is significantly reduced compared with the sample subjected to stripping at high temperature at atmospheric pressure.

EXAMPLE 3

Comparison of Atmospheric Stripping at High Temperature Versus Vacuum Stripping at Low Temperature of the Organic Phase The following experiments were performed to compare the ester content of organic phase samples which were subjected to either atmospheric stripping at high temperature or vacuum stripping at low temperature. The ester content of each sample was determined as described in Example 2. A sample of the organic phase (550 mls) prepared as described in Example 1 was distilled by pumping the sample into a one-liter three-neck round bottom flask equipped with a distillation head, a condenser, a mechanical stirrer and a thermocouple, and heating the sample up to a temperature of 150° C. at atmospheric pressure. A sample of the product obtained from atmospheric stripping was collected and the atmospheric stripping experiment was then continued by pumping fresh feed in for another 2.75 hours at a temperature of 150° C. A sample of the stripped product remaining in the pot after the addition of feed was complete was analyzed for ester content.

A sample of the organic phase (247.63 grams) prepared as described in Example 1 was vacuum distilled by charging the sample to a flask and attaching the flask to a rotary evaporator. The contents of the flask were then evaporated under vacuum at a temperature of 70° C. and a vacuum of 120 torr for about 1 hour. A sample of the product remaining from evaporation was collected and analyzed for ester content.

A portion of the vacuum distilled product as described above was then heated to 150° C. for 1 hour to remove residual volatiles. A sample was collected and analyzed for ester content. The results of these experiments are shown in Table 2 below.

TABLE 2

| SAMPLE CONDITIONS | PERCENT METHYL ESTER | PERCENT ETHYL ESTER | PERCENT HIGHER ESTERS |
|---|---|---|---|
| Control* | 1.7 | 0.6 | 0.5 |
| Distillation up to 150° C. at atmospheric pressure | 0.3 | 0.14 | 0.28 |
| Continuation of distillation at 137–150° C. at atmospheric pressure | 1.4 | 0.6 | 0.7 |
| Vacuum distillation at 70° C. and 120 torr | 0.2 | 0.05 | 0.08 |
| Vacuum distillation at 70° C. and 120 torr followed by heating to 150° C. at atmospheric pressure for 1 hour | 0.2 | 0.1 | 0.3 |

*Control - Sample of organic phase prepared as described in Example 1 which was sent through a heat loop heated to 150° C. and then sent to an atmospheric flash tank.

As shown in Table 2, continued atmospheric stripping at 150° C. increased the ester content of the organic phase to a value similar to that obtained for the control sample (heat loop at 150° C./atmospheric flash tank) whereas vacuum distillation alone or followed by evaporation at 150° C. significantly reduced the ester content of the organic phase.

EXAMPLE 4

Comparison of Atmospheric Stripping Versus Vacuum Stripping of the Organic Phase at Low Temperatures The following experiments were performed to compare the ester content of organic phase samples subjected to 1) atmospheric stripping at 90 and 115° C. or 2) vacuum stripping at low temperature.

A sample of organic phase (739.1 grams) prepared as described in Example 1 was charged to a one-liter four-neck flask equipped with a distillation head, a condenser, a mechanical stirrer and a thermocouple. The contents of the flask were heated with stirring up to a temperature of 90° C. at atmospheric pressure and held there for about 1 hour. The partially stripped product (434.0 grams) was then transferred to a one liter round bottom flask which was attached to a rotary evaporator. The contents of the flask were then evaporated under vacuum at a temperature of 85° C. and a vacuum of 100 torr to remove residual volatiles present in the product to give 229.0 grams of material. A sample of the distilled evaporated product was collected and analyzed for ester content.

A second sample of the same organic phase (526.0 grams) as referenced above was charged to a flask and evaporated under vacuum using a rotary evaporator at a temperature of 80° C. and a vacuum of 100 torr. The product (174.0 grams) obtained from evaporation was collected and analyzed for ester content.

A third sample of the same organic phase (679.5 grams) as referenced above, was charged to a one-liter four-neck flask equipped with a distillation head, a condenser, a mechanical stirrer and a thermocouple and distilled by heating the sample with stirring up to a temperature of 115° C. at atmospheric pressure and holding it there for one hour.

The product obtained from distillation was then stripped under vacuum using a rotary evaporator (80° C./100 torr) to further reduce volatiles remaining in the sample. A sample of the product obtained from evaporation was analyzed for ester content. The ester content of each sample was determined as described in Example 2. The results from the above experiments are listed in Table 3 below.

TABLE 3

| SAMPLE - CONDITIONS | PERCENT METHYL ETHYL | PERCENT ETHYL ESTER | PERCENT HIGHER ESTERS |
|---|---|---|---|
| Control* | 2.0 | 0.6 | 0.4 |
| Distillation at 90° C. and atmospheric pressure followed by vacuum distillation at 85° C. and 100 torr | 0.4 | 0.14 | 0.09 |
| Vacuum distillation at 80° C. and 100 torr | 0.3 | 0.06 | 0.06 |
| Distillation at 115° C. and atmospheric pressure followed by vacuum distillation at 80° C. and 100 torr | 0.3 | 0.15 | 0.33 |

*Control is the same as defined in Table 2.

The results in Table 3 show that atmospheric stripping at low temperature and vacuum stripping at low temperature and vacuum significantly reduced the ester content of the sample compared with that of the control sample. The lowest ester content was obtained by vacuum distillation of the organic phase sample.

EXAMPLE 5

Atmospheric Stripping Using An Atmospheric Pressure Pre-Stripping Column

An atmospheric pressure pre-stripping column was constructed to determine whether a stripping column could be utilized to remove alkanols from the organic phase to produce free fatty acids having a low ester content and high acid value.

The stripping equipment consisted of a 250 ml three-neck flask equipped with a magnetic stirrer, a heating mantel, a pot thermometer with temperature controller, a 26 mm I.D. adiabetic column with 14 inches of 7 mm Raschig Ring packing and a Claisen head with an addition funnel on one arm and a short path head on the other. The whole system was insulated.

Dichloroethane (100.0 grams) was charged to the pot of the stripping system and volatiles (66.06 grams) consisting of 92% dichloroethane, 5.0% methanol and 2.5% water were charged to a flask which was heated to 65° C. When the temperature of the volatiles reached 65° C., an organic phase sample which was vacuum stripped and steam sparged as described in Example 7 below was added to the flask, and the mixture was heated to 65° C. and then charged to the addition funnel of the stripping system.

The dichloroethane was heated to a pot temperature of 84° C. and the volatiles-organic phase mixture was added to the top of the column in a countercurrent manner. The pot temperature was maintained at 90 to 93° C. during the addition and the distillate was taken off as strippings (52.9%). After the volatiles-organic phase mixture was added the stripping column was removed and the remaining volatiles removed at 150° C. at atmospheric pressure to give distillate (18.1%) and product (20.3%). A sample of each material was analyzed for ester content and acid value as described in Example 2. The results from this experiment are shown in Table 4 below.

TABLE 4

| SAMPLE | PER-CENT METHYL ESTER | PER-CENT HIGHER ESTERS | PER-CENT ETHY-LENE DI-CHLOR-IDE | ACID VALUE | ACID VALUE (COR-RECTED FOR DI-CHLO-ETHANE) |
|---|---|---|---|---|---|
| Control* | 2.0 | 0.6 | trace | 189.3 | 189.3 |
| Organic phase-vacuum stripped and steam sparged | 0.4 | 0.9 | trace | 195.2 | 195.2 |
| Product using atmospheric pressure pre-stripping column | 0.6 | 0.9 | 6.7 | 180.7 | 193.7 |

*Control is the same as defined in Table 2.

As seen from Table 4, distillation of the aforementioned mixture containing fatty acids, methanol, and dichloroethane using an atmospheric pre-stripping column resulted in recovery of fatty acids having a higher acid value (193.7) than that obtained in the control sample, but lower than the vacuum stripped material.

EXAMPLE 6

Atmospheric and Vacuum Stripping of Organic Phase at Low Temperature Followed by Evaporation at High Temperature The following experiments were performed to determine whether the ester content of organic phase samples subjected to distillation at low temperatures would remain low if the samples were then subjected to an atmospheric flash tank (150° C.) to further reduce volatiles remaining in the sample.

A sample of the organic phase (1210.1 grams) prepared as described in Example 1 was distilled by charging the sample to a 2 liter flask equipped for distillation as described in Example 1, heating the contents of the flask up to a temperature of 90° C. at atmospheric pressure, and then holding for about 1 hour. The material was then vacuum distilled. A sample of the product obtained from this distillation was collected and analyzed for ester content.

A sample of the organic phase prepared as set forth in Example 1 was charged to a flask and evaporated under vacuum using a rotary evaporator at a temperature of 86° C. and a vacuum of 50 torr. The product obtained from evaporation was collected and analyzed for ester content. The experiment was repeated using another sample of organic phase (703.34 grams) and a sample of the product obtained from this evaporation was collected and analyzed for ester content.

The two products obtained by vacuum stripping as described above were charged to a 2-liter 4-neck flask equipped for distillation and heated to 150° C. at atmospheric pressure. A sample was collected and analyzed for ester content.

Subsequently, the remainder of the product obtained from atmospheric stripping at 90° C. as described above was added to the vacuum distilled product at 150° C. The volatiles were then stripped off during the addition while heating at 150° C. A sample of the product obtained from distillation was analyzed for ester content. The results of the above experiments are shown in Table 5.

TABLE 5

| SAMPLE - CONDITIONS | PERCENT METHYL ETHYL | PERCENT ETHYL ESTER | PERCENT HIGHER ESTERS |
|---|---|---|---|
| Control* | 1.7 | 0.6 | 0.5 |
| Distillation at 90° C. at atmospheric pressure | 0.3 | 0.1 | 0.1 |
| Vacuum distillation at 86° C. and 50 torr | 0.2 | 0.02 | 0.04 |
| Product obtained from vacuum distillation followed by heating up to 150° C. | 0.4 | 0.1 | 0.1 |
| Products obtained from vacuum distillation combined with product obtained from distillation at 90° C. at atmospheric pressure - Combined residues heated at 150° C. at atmospheric pressure. | 0.3 | 0.2 | 0.6 |

*Control is the same as defined in Table 2.

The data shown in Table 5 indicate that if alkanol is removed from the organic phase at low temperature and then volatiles are removed from the organic phase using an atmospheric flash tank at 150° C., the ester content of the resultant fatty acid product remains low. However, higher boiling alkanols present are not removed at lower temperature so the ester content does rise.

EXAMPLE 7

Preparation of Dimerized Fatty Acids Having High Acid Value

A sample of the organic phase (81.72 kilograms) prepared as described in Example 1 was placed in a reactor and vacuum stripped at a temperature of 50° C. and a vacuum of 50 torr. After the volatiles had been removed the product was steam sparged for one hour at a temperature of 64° C. and a vacuum of 50 torr. A sample of the vacuum/steam stripped product was analyzed for acid value (198.5). NMR analysis showed 0.6% methyl ester, 0.3% higher esters, and 0.06% dichloroethane.

A sample (6.69 kilograms) of vacuum/steam stripped product was then steam sparged to remove the remaining dichloroethane by heating the sample to a temperature of 110° C. and starting a steam sparge. The temperature was allowed to rise to 120° C. and the material was held at this temperature for 20 minutes. The steam-sparged sample was then cooled to about 100° C. and filtered using gravity filtration (Reeve Angel, folded circles Grade 802). NMR analysis showed 0.5% methyl ester, 0.8% higher ester and no dichloroethane.

A portion of the filtered material (1000.0 grams) was then subjected to solvent separation to separate saturated fatty acids from unsaturated fatty acids by cooling the filtered material to about −7.0° C. in the presence of 95% acetone in water. The solids which precipitated from the liquid were filtered out. The solids and liquid were then rotoevaporated to remove the acetone. The solid precipitate containing saturated fatty acids and liquid containing unsaturated fatty acids were collected and samples analyzed for acid value. The acid value of the solids were 195.3 and for the liquid 192.2.

A portion of the liquid (759.4 grams) obtained from solvent separation was vacuum distilled taking a heart cut at 198 to 220° C. and 0.8 torr. The heart cut contained mainly unsaturated fatty acids. A sample from each distillation cut was collected and analyzed for acid value.

A portion of the heart cut containing unsaturated fatty acids (500.0 grams) was dimerized by heating the distillate together with Engelhard F-100 Clay (Engelhard Industries, Jackson, MS, 22.5 grams), lithium carbonate (0.4 grams) and water (13.0 grams) in an autoclave at 250° C. at a pressure of 105 psig for 4 hours. Subsequently, the mixture was cooled to a temperature of 150° C. and the pressure was reduced to 10 psig. The material was further cooled to 100° C. at which point 75% $H_3PO_4$ (3.0 ml) and water (0.5 ml) were added to the mixture. The mixture was heated to 150° C. and held at that temperature for 5 minutes. The mixture was then cooled to 90° C. and filtered to remove the clay. A sample of the filtered dimerized mixture was analyzed for acid value and gave a 192.4 value.

A portion of the filtered dimerized fatty acids (376.92 grams) was vacuum distilled to a temperature of 290° C. at a vacuum of 96 m torr to remove the monomeric fatty acids as distillate. A sample of the monomer (distillate) and dimer (residue) were analyzed for acid value.

A portion of the distilled dimer (120.89 grams) was bleached by charging the dimer to a 4-neck 240 ml round bottomed flask. A thermometer, a stirrer, a nitrogen inlet and an outlet were attached to the flask and the system was purged with nitrogen, and then heated with stirring. At 90° C., 75% $H_3PO_4$ (0.12 gram) was added, and at 110° C., Grade T Filtrol (3.02 grams) was added. The mixture was stirred for 30 minutes at 110° C. and then filtered. A sample of the filtered bleached dimer was collected and analyzed for acid value and gave a 195.6 value.

TABLE 6

| PREPARATION OF DIMERIZED FATTY ACID | ACID VALUE |
|---|---|
| 1. Vacuum Stripping | 198.5 |
| 2. Solvent separation of vacuum stripped steam sparged material | |
| precipitate | 195.3 |
| liquid | 192.2 |
| 3. Vacuum distillation | |
| top cut | 247.3 |
| heart cut | 194.4 |
| residue | 71.5 |
| 4. Dimerization of unsaturated fatty acids | 192.4 |
| 5. Distillation of dimerized fatty acids | |
| monomer | 191.0 |
| dimer | 195.2 |
| 6. Bleached Dimer | 195.6 |

The data shown in Table 6 demonstrate that vacuum stripping reduced the ester content of the organic phase containing fatty acids which enabled the production of a composition comprising dimerized fatty acids having a high acid value.

EXAMPLE 8

Preparation of Isostearic Acid Having High Acid Value

Monomeric fatty acids obtained as distillate upon distilling the composition comprising dimerized fatty acids as described in Example 7, were hydrogenated by charging monomer (250.0 grams), Engelhard Code 26 nickel catalyst (4.17 grams, Engelhard Industries, Jackson, Miss.), and Code F20 clay catalyst (8.17 grams, Engelhard Industries, Jackson, Miss.) to an autoclave which was then sealed. The hydrogenation was conducted at a temperature of from 215 to 235° C. and at a pressure of 300 psi hydrogen for about 3.25 hours. The hydrogenated mixture was then filtered and a sample analyzed for acid value (195.0).

The filtered hydrogenated mixture was then subjected to solvent separation using 91% methanol to separate solid acids (stearic acid) from liquid (isostearic acid) using the following procedure. The sample (35.0 grams) and solvent (65.0 grams) were poured into a crystallizing bucket and cooled to −10° C. The crystalline precipitate was filtered and washed with a diluted, cold methanol solution. Subsequently, methanol was removed from the solids and mother liquor by rotoevaporation. A sample of the resultant residues were analyzed for acid value. (solids=201.9, liquids=188.5).

A portion of the liquid fraction obtained from solvent separation was charged to a 3-neck round bottom flask equipped for vacuum distillation and vacuum distilled at a vapor temperature up to 136° C. and a pressure of 0.9 torr to obtain a top cut, and then the product cut was taken up to a pot temperature of 200° C. at 0.9 torr. The product cut contained mainly isostearic acid. A sample from each cut was analyzed for acid value. The acid value for each sample is shown in Table 7 below.

TABLE 7

| SAMPLE | ACID VALUE |
|---|---|
| Hydrogenated Monomer | 195.0 |
| Solvent Separation of Hydrogenated Monomer | |
| solids | 201.9 |
| liquids | 188.5 |
| Distillation of Liquid Fraction | |
| top cut | 141.8 |
| product cut | 193.7 |
| residue | 136.9 |

As seen from Table 7, vacuum stripping of the organic phase containing fatty acids enabled the production of isostearic acid (product cut) having a high acid value.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

We claim:

1. A method for recovering free fatty acids from an alkanol-containing solution of the fatty acids which comprises distilling the alkanol-containing solution at a temperature from about 35° C. to about 90° C. and a pressure from about 50 torr to about 150 torr to provide a product containing free fatty acids and a fatty acid ester content of not greater than about 0.5 weight percent.

2. The method of claim 1 wherein the alkanol-containing solution is selected from the group consisting of a vegetable oil distillate, animal oil distillate, vegetable oil deodorizer distillate and animal oil deodorizer distillate.

3. The method of claim 1 wherein the alkanol-containing solution is a vegetable oil deodorizer distillate.

4. The method of claim 1 wherein the temperature is from about 75 to about 90° C. and the pressure is from about 50 to about 100 torr.

5. The method of claim 1 wherein the alkanol-containing solution contains one or more alkanols selected from the group consisting of methanol, ethanol, propanol, isopropanol, butanol, isobutanol, pentanol and hexanol.

6. The method of claim 1 wherein the product is subjected to steam stripping to further reduce alkanol present therein.

7. The method of claim 1 wherein the product possesses an acid value of from about 194 to about 200.

8. The method of claim 1 wherein the product possesses a fatty acid ester content of not greater than about 0.1 weight percent.

9. The method of claim 1 wherein the product possesses an acid value of from about 196 to about 200.

10. The method of claim 1 wherein the free fatty acids are selected from the group consisting of unsaturated fatty acids, saturated fatty acids and mixtures thereof.

11. The method of claim 10 wherein the unsaturated fatty acids are selected from the group consisting of oleic acid, linolenic acid, brassidic acid, elaidic acid, palmitoleic acid, erucic acid and arachidonic acid and the saturated fatty acids are selected from the group consisting of palmitic acid and stearic acid.

12. The method of claim 1 wherein the free fatty acids comprise oleic acid.

13. A method for recovering free fatty acids from an alkanol-containing solution of the fatty acids which comprises distilling the alkanol-containing solution at a temperature from about 85° C. to about 120° C. at atmospheric pressure to provide a product containing free fatty acids and a fatty acid ester content of not greater than about 0.5 weight percent.

14. The method of claim 13 wherein the temperature is from about 90 to about 115° C.

15. The method of claim 13 wherein distilling of the alkanol-containing solution is carried out using an atmospheric stripping column.

16. A method of separating fatty acids from a composition containing at least one non-saponifiable component which comprises:
(a) subjecting the composition to saponification conditions in the presence of alkali metal hydroxide, alkanol and water to provide a mixture containing at least one non-saponified component and saponified fatty acids;
(b) separating the mixture by solvent extraction employing a solvent to provide a solvent-rich phase containing the non-saponified component(s) of the mixture and a raffinate phase containing the saponified fatty acids, alkanol, water, the balance of the solvent, and alkali metal hydroxide;
(c) acidifying the raffinate phase to provide an aqueous phase containing water, alkanol and alkali metal salt and an organic phase containing fatty acids, alkanol and solvent; and,
(d) distilling the organic phase at a temperature from about 35° C. to about 90° C. and a pressure from about 50 torr to about 150 torr to provide a product containing free fatty acids and a fatty acid ester content of not greater than about 0.5 weight percent.

17. The method of claim 16 wherein the product is subjected to steam stripping to further reduce solvent present therein.

18. The method of claim 16 wherein the non-saponified component is tocopherol.

19. The method of claim 16 wherein the free fatty acids are selected from the group consisting of unsaturated fatty acids, saturated fatty acids and mixtures thereof.

20. The method of claim 16 wherein the unsaturated fatty acids are selected from the group consisting of oleic acid, linolenic acid, brassidic acid, elaidic acid, palmitoleic acid, erucic acid and arachidonic acid and the saturated fatty acids are selected from the group consisting of palmitic acid and stearic acid.

21. The method of claim 16 wherein the free fatty acids comprise oleic acid.

22. The method of claim 16 wherein the alkanol is selected from the group consisting of methanol, ethanol, propanol, isopropanol, butanol, isobutanol, pentanol, hexanol and mixtures thereof.

23. The method of claim 22 wherein the alkanol is methanol.

24. The method of claim 16 wherein the solvent is a hydrocarbon solvent.

25. The method of claim 16 wherein the solvent is a halogenated solvent.

26. The method of claim 25 wherein the halogenated solvent is selected from the group consisting of chloroform, dichloromethane and dichloroethane.

27. The method of claim 16 wherein distilling the organic phase is carried out at a temperature of from about 75 to about 90° C. and a pressure of from about 50 to about 100 torr.

28. The method of claim 16 wherein the product possesses an acid value of from about 194 to about 200.

29. The method of claim 16 wherein the product possesses a fatty acid ester content of not greater than about 0.1 weight percent.

30. The method of claim 16 wherein the product possesses an acid value of from about 196 to about 200.

31. A method of separating fatty acids from a composition containing at least one non-saponifiable component which comprises:
(a) subjecting the composition to saponification conditions in the presence of alkali metal hydroxide, alkanol and water to provide a mixture containing at least one non-saponified component and saponified fatty acids;
(b) separating the mixture by solvent extraction employing a solvent to provide a solvent-rich phase containing the non-saponified component(s) of the mixture and a raffinate phase containing the saponified fatty acids, alkanol, water, the balance of the solvent, and alkali metal hydroxide;
(c) acidifying the raffinate phase to provide an aqueous phase containing water, alkanol and alkali metal salt and an organic phase containing fatty acids, alkanol and solvent; and,
(d) distilling the organic phase at a temperature of from about 85° C. to about 120° C. and at atmospheric pressure to provide a product containing free fatty acids and a fatty acid ester content of not greater than about 0.5 weight percent.

32. The method of claim 31 wherein the temperature is from about 90 to about 115° C.

33. The method of claim 31 wherein distilling the organic phase is carried out using an atmospheric stripping column.

* * * * *